(12) United States Patent
Steed et al.

(10) Patent No.: US 8,318,197 B2
(45) Date of Patent: *Nov. 27, 2012

(54) WOUND HEALING DEVICE AND METHOD

(75) Inventors: David L. Steed, Pittsburgh, PA (US); Randall G. Rupp, Swanton, VT (US); Howard C. Wessel, New Kensington, PA (US)

(73) Assignee: Stemnion, Inc., Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/374,825

(22) Filed: Jan. 17, 2012

(65) Prior Publication Data

US 2012/0184975 A1    Jul. 19, 2012

Related U.S. Application Data

(60) Provisional application No. 61/461,445, filed on Jan. 18, 2011, provisional application No. 61/461,951, filed on Jan. 25, 2011, provisional application No. 61/463,185, filed on Feb. 14, 2011.

(51) Int. Cl.

| A61F 13/00 | (2006.01) |
|---|---|
| A61F 15/00 | (2006.01) |
| A61L 15/00 | (2006.01) |
| A61L 15/16 | (2006.01) |
| C07K 14/00 | (2006.01) |
| A61K 35/14 | (2006.01) |
| A61K 38/18 | (2006.01) |

(52) U.S. Cl. ........ 424/443; 424/445; 424/446; 424/447; 530/350; 530/351; 530/380; 514/8.1; 514/8.2; 514/8.9; 602/42; 602/43; 602/48; 602/50

(58) Field of Classification Search ........................ None
See application file for complete search history.

(56) References Cited

U.S. PATENT DOCUMENTS

| 7,118,746 | B1 | 10/2006 | Naughton et al. |
| 8,088,732 | B2 * | 1/2012 | Marshall et al. ............... 514/8.1 |
| 2006/0115460 | A1 | 6/2006 | Naughton et al. |
| 2006/0222634 | A1 | 10/2006 | Clarke et al. |
| 2007/0160653 | A1 * | 7/2007 | Fischer et al. ................ 424/443 |
| 2008/0102104 | A1 | 5/2008 | Shalaby |
| 2008/0286323 | A1 | 11/2008 | Tornoe et al. |
| 2009/0054339 | A1 | 2/2009 | Marshall et al. |
| 2010/0144604 | A1 | 6/2010 | Marshall et al. |

OTHER PUBLICATIONS

Brown, G., et al., 1988, Ann Surg 208(6):788-794.
Pasternak, B., et al., 2008, 23:271-276, Int. J. Colorectal Dis.
Steed, D.L., et al., 2008, ePlasty Open Access Journal of Plastic Surgery, e18.

* cited by examiner

*Primary Examiner* — Christine J Saoud
*Assistant Examiner* — Jegatheesan Seharaseyon
(74) *Attorney, Agent, or Firm* — Linda O. Palladino; Gail M. Kemplex

(57) ABSTRACT

The invention is directed to a novel wound healing device. In particular, the invention is directed to a novel wound healing device comprising a suture or knitted mesh that has adsorbed onto it novel cellular factor-containing compositions (referred to herein as CFC), including Amnion-derived Cellular Cytokine Solution (referred to herein as ACCS) or Physiologic Cytokine Solutions (herein referred to as PCS), as well as methods of making and uses thereof.

7 Claims, No Drawings

WOUND HEALING DEVICE AND METHOD

CROSS-REFERENCE TO RELATED APPLICATIONS

This application claims priority under 35 USC §119(e) of U.S. Provisional Application Nos. 61/461,445, filed Jan. 18, 2011, 61/461,951, filed Jan. 25, 2011, and 61/463,185, filed Feb. 14, 2011, the entireties of which are incorporated herein by reference.

FIELD OF THE INVENTION

The field of the invention is directed to a novel wound healing device. In particular, the field of the invention is directed to a novel wound healing device comprising a suture or a knitted mesh that has adsorbed onto it novel cellular factor-containing compositions (referred to herein as CFC), such CFCs including conditioned medium compositions obtained from extraembryonic cytokine secreting cells (ECS cells), including Amnion-derived Cellular Cytokine Solution (referred to herein as ACCS) obtained from Amnion-derived Multipotent Progenitor (AMP) cells, and Physiologic Cytokine Solution (herein referred to as PCS), as well as methods of making and uses thereof.

BACKGROUND OF THE INVENTION

Protein-based therapeutics are typically more difficult to administer to patients than other pharmaceuticals. Because the efficacy of a protein is related to its shape, protein-based therapeutics cannot be subjected to conditions that could cause the unfolding, or denaturing, of the protein or proteins contained therein. Consequently, special care is necessary in the preparation, storage, and administration of protein-based therapeutics.

In addition to avoiding any denaturation of the protein, it is often desirable to be able to control the amount of the protein administered to a patient over time. This helps to avoid protein concentrations within the patient that are undesirably high or low or that fluctuate too much from a desired level, and instead helps maintain a steady level of the therapeutic in the patient. To address this, sustained-release (also known as controlled-release/timed-release, etc.) formulations for many therapeutics, including protein-based therapeutics, have been or are currently in development. Sustained-release protein-based therapeutics can be administered by a variety of methods, including but not limited to oral delivery of tablets or capsules, inhalation of powders, implantation, incorporation into a matrix, or topical application of an encapsulated therapeutic from which the protein is gradually released over time.

Surgical sutures are medical devices used to hold body tissues together after an injury or surgery. Most modern sutures are synthetic, including absorbable sutures made of, for example, polyglycolic acid, polylactic acid, polydioxanone or caprolactone, all of which are broken down by various processes including hydrolysis (polyglycolic acid) and proteolytic enzymatic degradation, and the non-absorbable sutures made of, for example, nylon, polyester, or polypropylene. Natural materials used to make sutures include silk and gut. Recently sutures have been coated with antimicrobial substances to reduce the chances of infection. In addition to being made of different materials, sutures come in very specific sizes ranging from #5 (a heavy "braided" suture suitable for orthopedic use) to #11-0 (a fine "monofilament" suture suitable for ophthalmic use). Sutures must be strong enough to hold the tissue securely but flexible enough to be knotted. They must also be hypoallergenic.

There are numerous advantages and disadvantages to both "monofilament" and "braided" sutures. Advantages of the monofilament suture include that it is very smooth and has a low friction in the tissues, the suture runs very easily through the tissues, several continuous stitches can be pulled easily through the tissue without causing damage to the tissue, the surface of the suture tends not to harbor infection-causing microorganisms so stitch abscesses are less common than with a braided suture, and the surface of the suture is less likely to attracts platelets than a braided suture, which reduces the incidence of thrombus formation. Disadvantages include that monofilament sutures are slippery for an assistant to hold, are slippery for knot tying, may kink or snap, require more throws for security than a braided suture, the knots may slip, which is a disadvantage when relying on a stitch not slipping but is actually an advantage when snugging down 2 throws of a knot, the knots may unravel, are intolerant of the twisting effect of a series of stitches, tend to form loops more than a braided suture, are more springy than a braided suture, and have more memory (e.g. resists being straightened if it has been coiled up in its packet) than braided sutures.

The main differences between a monofilament suture and a braided suture is the higher friction and higher compliance exhibited by the braided suture. Advantages of braided sutures include they are less slippery, they are easier to handle, they have less memory (e.g. stretching it will permanently remove most coils and zigzags), they are easier to knot, the knots tend not to slip, fewer throws are needed on knots, and their friction can be used to advantage in subcuticular stitches. Disadvantages include the increased friction means it does not run as easily as a monofilament suture, even with a single stitch, there is a danger of the pull to overcome friction causing damage to the tissues, pulling the braided suture through more than one stitch at a time is hazardous, except for a subcuticular stitch, there is more chance of infection lodging in the braided suture and not being accessible to antibiotics, particularly with a non-absorbable stitch.

In addition to classic sutures, knitted mesh prepared from copolymers of glycolide and lactide is also suitable for use in the methods of the invention. The mesh is particularly suitable to reduce or prevent hernia formation following surgery, in particular, abdominal surgery.

Many different suturing techniques exist. The most common technique is the simple interrupted stitch which is the simplest to perform and is called "interrupted" because the suture thread is cut between each individual stitch. The vertical and horizontal mattress stitches are also interrupted but are more complex and specialized for particular settings. The running or continuous stitch is quicker but risks failing if the suture is cut in just one place; the continuous locking stitch is a more secure version of the running or continuous stitch. The chest drain stitch and corner stitch are variations of the horizontal mattress stitch. Other stitches include the Figure 8 stitch and subcuticular stitch.

Applicants present herewith for the first time the instant invention whose object is to deliver in a controlled manner physiologically relevant growth factors and cytokines at physiologic levels to a wound by adsorbing the compositions onto a suture or a knitted mesh.

BRIEF SUMMARY OF THE INVENTION

It is an object of the instant invention to provide a novel wound healing device and methods for using the device. Such a wound healing device comprises a nonabsorbable or bioerodable braided suture or knitted mesh that has absorbed onto it novel cellular factor-containing compositions (referred to herein as CFC, including ACCS) or physiologic cytokine solutions (herein referred to as PCS). The CFC, including ACCS, or PCS, contain a complex and unique combination of and physiologic levels of wound healing cytokines and growth factors found naturally in the body. Bioerodable braided sutures or knitted mesh are able to breakdown over time in the body, whereas nonabsorbable sutures persist until removed. In accordance with the invention, the bioerodable braided sutures or knitted mesh are absorbed with the CFC, including ACCS, or PCS, which become trapped in the spaces between the braided filaments of the sutures or the knitted mesh. The CFC, including ACCS, or PCS, are then released into the local wound area over time as a result of a combination of the protein factor release by diffusion and/or the erosion of the bioerodable suture or knitted mesh. Thus, the wound healing compositions are delivered precisely to the wound area for maximal effect. Because the cellular factors are present in levels comparable to physiological levels found in the body, they are optimal for use in therapeutic applications which require intervention to support, initiate, replace, accelerate or otherwise influence biochemical and biological processes involved in the treatment and/or healing of an injury or wound or, in the case of a knitted mesh, prevent or reduce hernia formation. The cellular factors are also released slowly over time to provide a continual, consistent physiologic level of such factors to optimize healing and/or recovery. In addition, CFC, including ACCS, or PCS, can be formulated prior to their absorption onto the suture or knitted mesh. Such formulations may include sustained-release/controlled-release/time-release formulations or the addition of gelling or thickening agents to improve adsorption onto the suture or knitted mesh. Details on sustained-release formulations of CFC, including ACCS, or PCS, can be found in US-2009-0054339-A1, published Feb. 26, 2009, the contents of which is incorporated herein by reference. The CFC, including ACCS, or PCS may also have heparin added to them prior to soaking the suture, or the sutures may have heparin adsorbed onto them prior to soaking in the CFC, including ACCS, or PCS. Heparin is known to bind to may proteins have heparin binding motifs and may serve to effect a slow release of the proteins found in the CFC, including ACCS, or PCS. Further, the CFC, including ACCS, or PCS, may be lyophilized prior to absorption onto the suture. Such lyophilization may include the addition of other agents, for example collagen. An important feature of the novel wound healing device described herein in that it is the first device disclosed that is capable of delivering numerous wound healing factors (for example, VEGF, TIMP-1, TIMP-2, PDGF, TGFβ2, Angiogenin) simultaneously, slowly and at physiologic concentrations directly to the wound site.

Accordingly, a first aspect of the invention is a wound healing device comprising a cellular factor-containing composition (CFC) adsorbed onto a braided suture or knitted mesh.

In one embodiment of aspect one the CFC is Amnion-derived Cellular Cytokine Solution (ACCS).

In another embodiment of aspect one the ACCS is concentrated ACCS.

In still another embodiment of aspect one the CFC is physiologic cytokine solution (PCS).

In yet another embodiment of aspect one the PCS is concentrated PCS.

In another embodiment of aspect one the suture or knitted mesh is nonabsorbable or bioerodable.

In a specific embodiment of aspect one the bioerodable suture or knitted mesh is made of polyglycolic acid, polyglutamic acid, polydioxanone, polylactide or caprolactone, or combinations thereof. In another specific embodiment of aspect one the nonabsorbable suture is made of nylon, polyester, polypropylene, or silk.

In another specific embodiment of aspect one the CFC comprises physiologic concentrations of VEGF, TGFβ2, Angiogenin, PDGF, TIMP-1 and TIMP-2.

In a very specific embodiment of aspect one the physiologic concentration is ~5.0-16 ng/mL for VEGF, ~3.5-4.5 ng/mL for Angiogenin, ~100-165 pg/mL for PDGF, ~2.5-2.7 ng/mL for TGFβ2, ~0.68 μmL for TIMP-1 and 181.04 μg/mL for TIMP-2.

A second aspect of the invention is a kit comprising the wound healing device of aspect one.

A third aspect of the invention is a method of promoting wound healing in a subject in need thereof comprising suturing the wound with the wound healing device of aspect one.

In a particular embodiment of aspect three the suturing is continuous suturing of the wound.

A fourth aspect of the invention is a method for reducing or prevented hernia formation comprising placing the knitted mesh wound healing device of aspect one in a patient during surgery to reduce or prevent hernia formation following surgery.

A fifth aspect of the invention is a method for the delivery of a mixture of protein factors directly to a wound such that the protein factors are delivery simultaneously to the wound, the method comprising the step of applying the wound healing device of aspect one to the wound.

Definitions

As defined herein "isolated" refers to material removed from its original environment and is thus altered "by the hand of man" from its natural state.

As used herein, "enriched" means to selectively concentrate or to increase the amount of one or more materials by elimination of the unwanted materials or selection and separation of desirable materials from a mixture (i.e. separate cells with specific cell markers from a heterogeneous cell population in which not all cells in the population express the marker).

As used herein, the term "substantially purified" means a population of cells substantially homogeneous for a particular marker or combination of markers. By substantially homogeneous is meant at least 90%, and preferably 95% homogeneous for a particular marker or combination of markers.

The term "placenta" as used herein means both preterm and term placenta.

As used herein, the term "totipotent cells" shall have the following meaning. In mammals, totipotent cells have the potential to become any cell type in the adult body; any cell type(s) of the extraembryonic membranes (e.g., placenta). Totipotent cells are the fertilized egg and approximately the first 4 cells produced by its cleavage.

As used herein, the term "pluripotent stem cells" shall have the following meaning. Pluripotent stem cells are true stem cells with the potential to make any differentiated cell in the body, but cannot contribute to making the components of the extraembryonic membranes which are derived from the trophoblast. The amnion develops from the epiblast, not the trophoblast. Three types of pluripotent stem cells have been confirmed to date: Embryonic Stem (ES) Cells (may also be totipotent in primates), Embryonic Germ (EG) Cells, and Embryonic Carcinoma (EC) Cells. These EC cells can be isolated from teratocarcinomas, a tumor that occasionally occurs in the gonad of a fetus. Unlike the other two, they are usually aneuploid.

As used herein, the term "multipotent stem cells" are true stem cells but can only differentiate into a limited number of types. For example, the bone marrow contains multipotent stem cells that give rise to all the cells of the blood but may not be able to differentiate into other cells types.

As used herein, the term "extraembryonic cytokine-secreting cells" or "ECS cells" means a population of cells derived from the extraembryonic tissue which have the characteristic of secreting VEGF, Angiogenin, PDGF and TGFβ2 and the MMP inhibitors TIMP-1 and/or TIMP-2 at physiologically relevant levels in a physiologically relevant temporal manner into the extracellular space or into the surrounding culture media. ECS cells have not been cultured in the presence of any non-human animal materials, making them and cell products derived from them suitable for human clinical use as they are not xeno-contaminated. ECS cells may be selected from populations of cells and compositions described in this application and in US2003/0235563, US2004/0161419, US2005/0124003, U.S. Provisional Application Nos. 60/666,949, 60/699,257, 60/742,067, 60/813,759, U.S. application Ser. No. 11/333,849, U.S. application Ser. No. 11/392,892, PCTUS06/011392, US2006/0078993, PCT/US00/40052, U.S. Pat. No. 7,045,148, US2004/0048372, and US2003/0032179, the contents of which are incorporated herein by reference in their entirety. ECS cells have previously been referred to as TSE cells.

As used herein, the term "Amnion-derived Multipotent Progenitor cell" or "AMP cell" means a specific population of cells that are epithelial cells derived from the amnion. AMP cells have the following characteristics. They have not been cultured in the presence of any non-human animal materials, making them and cell products derived from them suitable for human clinical use as they are not xeno-contaminated. AMP cells are cultured in basal medium supplemented with human serum albumin. In a preferred embodiment, the AMP cells secrete the cytokines VEGF, Angiogenin, PDGF and TGFβ2 and the MMP inhibitors TIMP-1 and/or TIMP-2. The physiological range of the cytokine or cytokines in the unique combination is as follows: ~5-16 ng/mL for VEGF, ~3.5-4.5 ng/mL for Angiogenin, ~100-165 pg/mL for PDGF, ~2.5-2.7 ng/mL for TGFβ2, ~0.68 μg/mL for TIMP-1 and ~1.04 μg/mL for TIMP-2. The AMP cells may optionally express Thymosin β4. AMP cells grow without feeder layers, do not express the protein telomerase and are non-tumorigenic. AMP cells do not express the hematopoietic stem cell marker CD34 protein. The absence of CD34 positive cells in this population indicates the isolates are not contaminated with hematopoietic stem cells such as umbilical cord blood or embryonic fibroblasts. Virtually 100% of the cells react with antibodies to low molecular weight cytokeratins, confirming their epithelial nature. Freshly isolated amnion-derived cells, from which AMP cells are isolated, will not react with antibodies to the stem/progenitor cell markers c-kit (CD117) and Thy-1 (CD90). Several procedures used to obtain cells from full term or pre-term placenta are known in the art (see, for example, US 2004/0110287; Anker et al., 2005, Stem Cells 22:1338-1345; Ramkumar et al., 1995, Am. J. Ob. Gyn. 172: 493-500). However, the methods used herein provide improved compositions and populations of cells.

By the term "animal-free" when referring to certain compositions, growth conditions, culture media, etc. described herein, is meant that no non-human animal-derived materials, such as bovine serum, proteins, lipids, carbohydrates, nucleic acids, vitamins, etc., are used in the preparation, growth, culturing, expansion, storage or formulation of the certain composition or process. By "no non-human animal-derived materials" is meant that the materials have never been in or in contact with a non-human animal body or substance so they are not xeno-contaminated. Only clinical grade materials, such as recombinantly produced human proteins, are used in the preparation, growth, culturing, expansion, storage and/or formulation of such compositions and/or processes.

By the term "expanded", in reference to cell compositions, means that the cell population constitutes a significantly higher concentration of cells than is obtained using previous methods. For example, the level of cells per gram of amniotic tissue in expanded compositions of AMP cells is at least 50 and up to 150 fold higher than the number of amnion epithelial cells in the primary culture after 5 passages, as compared to about a 20 fold increase in such cells using previous methods. In another example, the level of cells per gram of amniotic tissue in expanded compositions of AMP cells is at least 30 and up to 100 fold higher than the number of amnion epithelial cells in the primary culture after 3 passages. Accordingly, an "expanded" population has at least a 2 fold, and up to a 10 fold, improvement in cell numbers per gram of amniotic tissue over previous methods. The term "expanded" is meant to cover only those situations in which a person has intervened to elevate the number of the cells.

As used herein, the term "passage" means a cell culture technique in which cells growing in culture that have attained confluence or are close to confluence in a tissue culture vessel are removed from the vessel, diluted with fresh culture media (i.e. diluted 1:5) and placed into a new tissue culture vessel to allow for their continued growth and viability. For example, cells isolated from the amnion are referred to as primary cells. Such cells are expanded in culture by being grown in the growth medium described herein. When such primary cells are subcultured, each round of subculturing is referred to as a passage. As used herein, "primary culture" means the freshly isolated cell population.

As used herein, "conditioned medium" is a medium in which a specific cell or population of cells has been cultured, and then removed. When cells are cultured in a medium, they may secrete cellular factors that can provide support to or affect the behavior of other cells. Such factors include, but are not limited to hormones, cytokines, extracellular matrix (ECM), proteins, vesicles, antibodies, chemokines, receptors, inhibitors and granules. The medium containing the cellular factors is the conditioned medium. Examples of methods of preparing conditioned media are described in U.S. Pat. No. 6,372,494 which is incorporated by reference in its entirety herein.

As used herein, the term "Amnion-derived Cellular Cytokine Solution" or "ACCS" means conditioned medium that has been derived from AMP cells that have been cultured in basal media supplemented with human serum albumin The term "physiological level" as used herein means the level that a substance in a living system is found and that is relevant to the proper functioning of a biochemical and/or biological process.

As used herein, the term "Physiologic Cytokine Solution" or "PCS" composition means a composition which is not cell-derived and which has physiologic concentrations of one or more factors selected from VEGF, Angiogenin, PDGF and TGFβ2 and at least one MMP inhibitor. Examples of suitable MMP inhibitors include but are not limited to TIMP-1 and TIMP-2. Details on PCS can be found in U.S. Publication No. US-2009-0054339-A1, the contents of which are incorporated herein by reference.

As used herein, the term "solution" as used in "Amnion-derived Cellular Cytokine Solution" means a liquid containing dispersed components, i.e. cytokines. The dispersed components may be fully solubilized, partially solubilized, suspended or otherwise dispersed in the liquid. Suitable liquids include, but are not limited to, water, osmotic solutions such as salt and/or sugar solutions, cell culture media, and other aqueous or non-aqueous solutions.

The term "lysate" as used herein refers to the composition obtained when cells, for example, AMP cells, are lysed and optionally the cellular debris (e.g., cellular membranes) is removed. This may be achieved by mechanical means, by freezing and thawing, by sonication, by use of detergents, such as EDTA, or by enzymatic digestion using, for example, hyaluronidase, dispase, proteases, and nucleases. In some instances, it may be desirable to lyse the cells and retain the cellular membrane portion and discard the remaining portion of the lysed cells.

As used herein, the term "pooled" means a plurality of compositions that have been combined to create a new composition having more constant or consistent characteristics as compared to the non-pooled compositions. For example, pooled ACCS have more constant or consistent characteristics compared to non-pooled ACCS. Examples of pooled compositions include "SP pools" (more than one ACCS collection/one placenta), "MP1 pools" (one ACCS collection/placenta, multiple placentas), and "MP2 pools" (more than one ACCS collection/placenta, multiple placentas).

As used herein, the term "substrate" means a defined coating on a surface that cells attach to, grown on, and/or migrate on. As used herein, the term "matrix" means a substance that cells grow in or on that may or may not be defined in its components. The matrix includes both biological and non-biological substances. As used herein, the term "scaffold" means a three-dimensional (3D) structure (substrate and/or matrix) that cells grow in or on. It may be composed of biological components, synthetic components or a combination of both. Further, it may be naturally constructed by cells or artificially constructed. In addition, the scaffold may contain components that have biological activity under appropriate conditions.

The term "cell product" or "cell products" as used herein refers to any and all substances made by and secreted from a cell, including but not limited to, protein factors (i.e. growth factors, differentiation factors, engraftment factors, cytokines, morphogens, proteases (i.e. to promote endogenous cell delamination, protease inhibitors), extracellular matrix components (i.e. fibronectin, etc.).

The term "therapeutically effective amount" means that amount of a therapeutic agent necessary to achieve a desired physiological effect (i.e. accelerate wound healing).

As used herein, the term "pharmaceutically acceptable" means that the components, in addition to the therapeutic agent, comprising the formulation, are suitable for administration to the patient being treated in accordance with the present invention.

As used herein, the term "therapeutic protein" includes a wide range of biologically active proteins including, but not limited to, growth factors, enzymes, hormones, cytokines, inhibitors of cytokines, blood clotting factors, peptide growth and differentiation factors.

As used herein, the term "tissue" refers to an aggregation of similarly specialized cells united in the performance of a particular function.

As used herein, the terms "a" or "an" means one or more; at least one.

As used herein, the term "adjunctive" means jointly, together with, in addition to, in conjunction with, and the like.

As used herein, the term "co-administer" can include simultaneous or sequential administration of two or more agents.

As used herein, the term "agent" means an active agent or an inactive agent. By the term "active agent" is meant an agent that is capable of having a physiological effect when administered to a subject. Non-limiting examples of active agents include growth factors, cytokines, antibiotics, cells, conditioned media from cells, etc. By the term "inactive agent" is meant an agent that does not have a physiological effect when administered. Such agents may alternatively be called "pharmaceutically acceptable excipients". Non-limiting examples include time release capsules and the like.

The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal, epidural, intracerebral and intrasternal injection or infusion.

The term "enteral administration" and "administered enterally" are art-recognized and refer to modes of administration other than enteral and topical administration, usually by oral or rectal routes.

The term "topical administration" and "administered topically" are art-recognized and refer to modes of administration other than parenteral and enteral administration, usually by application to the skin.

The term "adsorb" as used herein refers to the act of a liquid, gas, or a dissolved substance accumulating on the surface of a solid.

The terms "sustained-release", "extended-release", "time-release", "controlled-release", or "continuous-release" as used herein means an agent, typically a therapeutic agent or drug, that is released over time.

The terms "bioerodable" or "bioerosion" as used herein mean a combination of physical (i.e. dissolution) and chemical (i.e. chemical bond cleavage) processes that result in the breakdown of a substance.

The term "biodegradable" or "biodegradation" as used herein means a biological agent (i.e. an enzyme, microbe or cell) is responsible for the breakdown of a substance.

The terms "bioresporbable" or "bioabsorptable" as used herein mean the removal of a breakdown product by cellular activity (i.e. phagocytosis). The term "nonabsorbable" as used herein means that a substance is not broken down by a chemical process.

"Treatment," "treat," or "treating," as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition, i.e., arresting its development; (c) relieving and or ameliorating the disease or condition, i.e., causing regression of the disease or condition; or (d) curing the disease or condition, i.e., stopping its development or progression. The population of subjects treated by the methods of the invention includes subjects suffering from the undesirable condition or disease, as well as subjects at risk for development of the condition or disease.

As used herein, a "wound" is any disruption, from whatever cause, of normal anatomy (internal and/or external anatomy) including but not limited to traumatic injuries such as mechanical (i.e. contusion, penetrating), thermal, chemical, electrical, concussive and incisional injuries; elective injuries such as operative surgery and resultant incisional hernias, fistulas, etc.; acute wounds, chronic wounds, infected wounds, and sterile wounds, as well as wounds associated with disease states (i.e. ulcers caused by diabetic neuropathy or ulcers of the gastrointestinal or genitourinary tract). A wound is dynamic and the process of healing is a continuum requiring a series of integrated and interrelated cellular processes that begin at the time of wounding and proceed beyond initial wound closure through arrival at a stable scar. These cellular processes are mediated or modulated by humoral substances including but not limited to cytokines, lymphokines, growth factors, and hormones. In accordance with the subject invention, "wound healing" refers to improving, by some form of intervention, the natural cellular processes and humoral substances of tissue repair such that healing is faster, and/or the resulting healed area has less scaring and/or the wounded area possesses tissue strength that is closer to that of uninjured tissue and/or the wounded tissue attains some degree of functional recovery.

As used herein the term "standard animal model for wound healing" refers to any art-accepted animal model for wound healing in which the compositions of the invention exhibit efficacy as measured by accelerated wound healing. Non-limiting examples of suitable models are described in Hayward P G, Robson M C: Animal models of wound contraction. In Barbul A, et al: Clinical and Experimental Approaches to Dermal and Epidermal Repair: Normal and Chronic Wounds. John Wiley & Sons, New York, 1990; Del-Becarro, et al: The use of specific thromboxane inhibitors to preserve the dermal microcirculation after burning. Surgery 87: 137-141, 1980; Robson, et al: Increasing dermal perfusion after burning by decreasing thromboxane production. J Trauma 20: 722-725, 1980; Polo, et al: An in vivo model of human proliferative scar. J Surg Res 74: 187-195, 1998.). Skilled artisans are aware of other suitable models.

DETAILED DESCRIPTION

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

Obtaining and Culturing of Cells

ECS Cells—Various methods for isolating cells from extraembryonic tissue, which may then be used to produce the ECS cells of the instant invention are described in the art (see, for example, US2003/0235563, US2004/0161419, US2005/0124003, U.S. Provisional Application Nos. 60/666,949, 60/699,257, 60/742,067, 60/813,759, U.S. application Ser. No. 11/333,849, U.S. application Ser. No. 11/392,892, PCTUS06/011392, US2006/0078993, PCT/US00/40052, U.S. Pate. No. 7,045,148, US2004/0048372, and US2003/0032179).

Identifying ECS Cells—Once extraembryonic tissue is isolated, it is necessary to identify which cells in the tissue have the characteristics associated with ECS cells (see definition above). For example, cells are assayed for their ability to secrete VEGF, Angiogenin, PDGF and TGFβ2 and the MMP inhibitors TIMP-1 and/or TIMP-2 into the extracellular space or into surrounding culture media. In some instances, it may be difficult or impossible to detect certain factors using standard assays. This may be because certain factors are secreted by the cells at physiological levels that are below the level of detection by the assay methods. It may also be that the factor(s) is being utilized by the ECS cell and/or by other local cells, thus preventing accumulation at detectable levels using standard assays. It is also possible that the temporal manner in which the factors are secreted may not coincide with the timing of sampling.

AMP cell compositions are prepared using the steps of a) recovery of the amnion from the placenta, b) dissociation of the epithelial cells from the amniotic membrane using a protease, c) culturing of the cells in a basal medium with the addition of a naturally derived or recombinantly produced human protein (i.e. human serum albumin) and no non-human animal protein; d) selecting AMP cells from the epithelial cell culture, and optionally e) further proliferation of the cells, optionally using additional additives and/or growth factors (i.e. recombinant human EGF). Details are contained in US Publication No. 2006-0222634-A1, which is incorporated herein by reference.

Culturing of the AMP Cells—The cells are cultured in a basal medium. Such medium includes, but is not limited to, EPILIFE® culture medium for epithelial cells (Cascade Biologicals), OPTI-PRO™ serum-free culture medium, VP-SFM serum-free medium, IMDM highly enriched basal medium, KNOCKOUT™ DMEM low osmolality medium, 293 SFM II defined serum-free medium (all made by Gibco; Invitrogen), HPGM hematopoietic progenitor growth medium, Pro 293S-CDM serum-free medium, Pro 293A-CDM serum-free medium, UltraMDCK™ serum-free medium (all made by Cambrex), STEMLINE® T-cell expansion medium and STEMLINE® II hematopoietic stem cell expansion medium (both made by Sigma-Aldrich), DMEM culture medium, DMEM/F-12 nutrient mixture growth medium (both made by Gibco), Ham's F-12 nutrient mixture growth medium, M199 basal culture medium (both made by Sigma-Aldrich), and other comparable basal media. Such media should either contain human protein or be supplemented with human protein. As used herein a "human protein" is one that is produced naturally or one that is produced using recombinant technology. "Human protein" also is meant to include a human derivative or preparation thereof, such as human serum, which contains human protein. In specific embodiments, the basal media is IMDM highly enriched basal medium, STEMLINE® T-cell expansion medium or STEMLINE® II hematopoietic stem cell expansion medium, or OPTI-PRO™ serum-free culture medium, or combinations thereof and the human protein is human serum albumin is at least 0.5% and up to 10%. In particular embodiments, the human serum albumin is from about 0.5 to about 2%. In a specific embodiment the human albumin is at 0.5%. The human albumin may come from a liquid or a dried (powder) form and includes, but is not limited to, recombinant human serum albumin, PLASBUMIN® normal human serum albumin and PLASMANATE® human blood fraction (both made by Talecris Biotherapeutics).

In a most preferred embodiment, the cells are cultured using a system that is free of non-human animal products to avoid xeno-contamination. In this embodiment, the culture medium is IMDM highly enriched basal medium , STEM-LINE® T-cell expansion medium or STEMLINE® II hematopoietic stem cell expansion medium, OPTI-PRO™ serum-free culture medium, or DMEM culture medium, with human serum albumin (i.e. PLASBUMIN® normal human serum albumin) added up to amounts of 10%.

The invention further contemplates the use of any of the above basal media wherein animal-derived proteins are replaced with recombinant human proteins and animal-derived serum, such as BSA, is replaced with human serum albumin. In preferred embodiments, the media is serum-free in addition to being animal-free.

Optionally, other factors are used. In one embodiment, epidermal growth factor (EGF) at a concentration of between 0-1 µg/mL is used. In a preferred embodiment, the EGF concentration is around 10-20 ng/mL. All supplements are clinical grade.

Generation of CFC, including ACCS

ECS conditioned medium- is obtained as described below for ACCS, except that ECS cells are used.

Generation of ACC—The AMP cells of the invention can be used to generate ACCS. In one embodiment, the AMP cells are isolated as described herein and $1\times10^6$ cells/mL are seeded into T75 flasks containing between 5-30 mL culture medium, preferably between 10-25 mL culture medium, and most preferably about 10 mL culture medium. The cells are cultured until confluent, the medium is changed and in one embodiment the ACCS is collected 1 day post-confluence. In another embodiment the medium is changed and ACCS is collected 2 days post-confluence. In another embodiment the medium is changed and ACCS is collected 4 days post-confluence. In another embodiment the medium is changed and ACCS is collected 5 days post-confluence. In a preferred embodiment the medium is changed and ACCS is collected 3 days post-confluence. In another preferred embodiment the medium is changed and ACCS is collected 3, 4, 5, 6 or more days post-confluence. Skilled artisans will recognize that other embodiments for collecting ACCS from AMP cell cultures, such as using other tissue culture vessels, including but not limited to cell factories, flasks, hollow fibers, or suspension culture apparatus, or collecting ACCS from sub-confluent and/or actively proliferating cultures, are also contemplated by the methods of the invention. It is also contemplated by the instant invention that the ACCS be cryopreserved following collection. It is also contemplated by the invention that ACCS be lyophilized following collection. It is also contemplated by the invention that ACCS be formulated for sustained-release following collection. Skilled artisans are familiar with cryopreservation lyophilization, and sustained-release formulation methodologies.

The ACCS of the invention is characterized by assaying for physiologically relevant cytokines secreted in the physiologically relevant range of ~5-16 ng/mL for VEGF, ~.3.5-4.5 ng/mL for Angiogenin, ~100-165 pg/mL for PDGF, ~2.5-2.7 ng/mL for TGFβ2, ~0.68 µg mL for TIMP-1 and ~1.04 µg/mL for TIMP-2.

It is also contemplated by the invention that ACCS, including pooled ACCS, be concentrated prior to use. The appropriate level of concentration required will be dependent upon the intended use and therefore will need to be empirically determined.

Generation of PCS

A non-cellular derived form of CFC termed Physiologic Cytokine Solution (PCS) is generated by combining physiological levels of VEGF, Angiogenin, PDGF, TGFβ2, TIMP-1 and TIMP-2, in a carrier. The physiological levels for these cytokines are the same as those found in ACCS. Suitable carriers include normal saline, PBS, lactated Ringer's solution, cell culture medium, etc. Such compositions are suitable for cryopreservation, lyophilization, sustained-release formulation, and the like.

It is contemplated that PCS may be produced such that it contains more concentrated levels of the factors than those found in CFC, including ACCS, and that it may be subsequently diluted with appropriate diluent prior to use. Appropriate diluents include, without limitation, normal saline, PBS, lactated Ringer's solution, cell culture media, conditioned cell culture media, water, and the like. Such dilutions may be 1:2, 1:3, 1:4, 1:5, 1:10, 1:100, etc. The appropriate concentrations and dilutions required will be dependent upon the intended use and therefore will need to be empirically determined.

The compositions of the invention can be prepared in a variety of ways depending on the intended use of the compositions. For example, a composition useful in practicing the invention may be a liquid comprising an agent of the invention, i.e. CFC, including ACCS, or PCS, in solution, in suspension, or both (solution/suspension). The term "solution/suspension" refers to a liquid composition where a first portion of the active agent is present in solution and a second portion of the active agent is present in particulate form, in suspension in a liquid matrix. A liquid composition also includes a gel. The liquid composition may be aqueous or in the form of an ointment, salve, cream, or the like.

An aqueous suspension or solution/suspension useful for practicing the methods of the invention may contain one or more polymers as suspending agents. Useful polymers include water-soluble polymers such as cellulosic polymers and water-insoluble polymers such as cross-linked carboxyl-containing polymers. An aqueous suspension or solution/suspension of the present invention is preferably viscous or muco-adhesive, or even more preferably, both viscous and muco-adhesive.

Alternative Formulation of CFC, including ACCS, or PCS

The CFC, including ACCS, or PCS, may be formulated as sustained-release/controlled-release/timed-release compositions. Skilled artisans are familiar with methodologies to create such compositions of therapeutic agents, including protein-based therapeutic agents such as CFC, including ACCS, or PCS.

Sustained-release/controlled-release/timed-release CFC, including ACCS, or PCS may be made by any of the methods described herein. For example, multivesicular liposome formulation technology is useful for the sustained-release of protein and peptide therapeutics. Qui, J., et al, (ACTA Pharmacol Sin, 2005, 26(11):1395-401) describe this methodology for the formulation of sustained-release interferon alpha-2b. Vyas, S. P., et al, (Drug Dev Ind Pharm, 2006, 32(6):699-707) describe encapsulating pegylated interferon alpha in multivesicular liposomes. CFC, including ACCS, or PCS are suitable for use in multivesicular liposome sustained-release formulation.

Nanoparticle technology is also useful for creating CFC, including ACCS, or PCS sustained-release/controlled-release/timed-release compositions. For example, Packhaeuser, C. B., et al, (J Control Release, 2007, 123(2):131-40) describe biodegradable parenteral depot systems based on insulin loaded dialkylaminoalkyl-amine-poly(vinyl alcohol)- g-poly(lactide-co-glycolide) nanoparticules and conclude that nanoparticle-based depots are suitable candidates for the design of controlled-release devices for bioactive macromolecules (i.e. proteins). Dailey, L. A., et al, (Pharm Res 2003, 20(12):2011-20) describe surfactant-free, biodegradable nanoparticles for aerosol therapy which is based on the branched polymers DEAPA-PVAL-g-PLGA and conclude that DEAPA-PVAL-g-PLGA are versatile drug delivery systems. CFC, including ACCS, or PCS are suitable for use in nanoparticle-based sustained-release formulations.

Polymer-based sustained-release formulations are also very useful. Chan, Y. P., et al, (Expert Opin Drug Deliv, 2007, 4(4):441-51) provide a review of the Medusa system (Flamel Technologies), which is used for sustained-release of protein and peptide therapies. Thus far, the Medusa system has been applied to subcutaneous injection of IL-2 and IFN-alpha(2b), in animal models (rats, dogs, monkeys), and in clinical trials in renal cancer (IL-2) and hepatitis C (IFN-alpha(2b)) patients. Chavanpatil, M. D., et al, (Pharm Res, 2007, 24(4): 803-10) describe surfactant-polymer nanoparticles as a novel platform for sustained and enhanced cellular delivery of water-soluble molecules. Takeuchi, H., et al, (Adv Drug Deliv Res, 2001, 47(1):39-54) describe mucoadhesive nanoparticulate systems for peptide drug delivery, including liposomes and polymeric nanoparticles. Wong, H. L., et al, (Pharm Res, 2006, 23(7):1574-85) describe a new polymer-lipid hybrid system which has been shown to increase cytotoxicity of doxorubicin against multidrug-resistant breast cancer cells. CFC, including ACCS, or PCS are suitable for use in the aforementioned sustained-release formulation methodologies.

In addition, other sustained-release methodologies familiar to skilled artisans, while not specifically described herein, are also suitable for use with the CFC, including ACCS, or PCS compositions.

Pharmaceutical Compositions—The present invention provides pharmaceutical compositions of CFC, including ACCS, or PCS and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the composition is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Examples of suitable pharmaceutical carriers are described in "Remington's Pharmaceutical Sciences" by E. W. Martin, and still others are familiar to skilled artisans.

The pharmaceutical compositions of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Treatment Kits—The invention also provides for an article of manufacture comprising packaging material and a pharmaceutical composition of the invention contained within the packaging material, wherein the pharmaceutical composition comprises compositions of CFC, including ACCS, or PCS, and nonabsorbable or bioerodable braided suture or knitted mesh (the Wound Healing Device). The packaging material comprises a label or package insert which indicates that the Wound Healing Device can be used for promoting wound healing and/or reducing or preventing hernia formation in a subject in need thereof.

One of skill in the art may readily determine the appropriate concentration, or dose, of the CFC, including ACCS, or PCS, for a particular purpose. The skilled artisan will recognize that a preferred dose is one which produces a therapeutic effect, such as promoting wound healing and/or reducing or preventing hernia formation, in a patient in need thereof. Of course, proper doses of the CFC, including ACCS, or PCS, will require empirical determination at time of use based on several variables including but not limited to the severity and type of injury or wound being treated; patient age, weight, sex, health; other medications and treatments being administered to the patient; and the like. One of skill in the art will also recognize that number of doses (dosing regimen) to be administered needs also to be empirically determined based on, for example, severity and type of disease, injury, disorder or condition being treated. In a preferred embodiment, one dose is sufficient.

The present invention provides a method of promoting wound healing and/or reducing or preventing hernia formation by administering a therapeutically effective dose of CFC, including ACCS, or PCS, to a subject via the Wound Healing Device. By "therapeutically effective amount" is meant the dose of CFC, including ACCS, or PCS, which is sufficient to elicit a therapeutic effect. Thus, the concentration of CFC, including ACCS, or PCS, in an administered dose unit in accordance with the present invention is effective in, for example, promoting wound healing and/or reducing or preventing hernia formation.

In further embodiments of the present invention, it may be desirable to co-administer other agents, including active agents and/or inactive agents, with the Wound Healing Device to promote wound healing and/or reducing or preventing hernia formation. Active agents include but are not limited to cytokines, chemokines, antibodies, inhibitors, antibiotics, anti-fungals, anti-virals, immunosuppressive agents, other cell types, and the like. Inactive agents include carriers, diluents, stabilizers, gelling agents, thickening agents (i.e. human serum albumin, hyaluronic acid), delivery vehicles, ECMs (natural and synthetic), scaffolds, collagen, and the like. When the Wound Healing Device is administered conjointly with other pharmaceutically active agents, even less of the CFC, including ACCS, or PCS, in the Wound Healing Device may be needed to be therapeutically effective.

The timing of administration of the Wound Healing Device will depend upon the type and severity of the injury or wound being treated. In a preferred embodiment, the Wound Healing Device is administered as soon as possible after the injury or wound occurs.

Skilled artisans will recognize that any and all of the standard methods and modalities for treating injuries and wounds currently in clinical practice and clinical development are suitable for practicing the methods of the invention. Routes of administration, formulation, co-administration with other agents (if appropriate) and the like are discussed in detail elsewhere herein.

Exemplary Therapeutic Uses of the Wound Healing Device
Wound Healing—The Wound Healing Device of the present invention is effective in accelerating wound healing of wounds caused by a number of sources, including but not limited to incisional, compression, thermal, penetrating, concussive, acute, chronic, infected, and sterile injuries. The instant invention is based upon the discovery that ACCS, which is adsorbed onto the suture or knitted mesh, can accelerate the wound healing process for all wound types. Accordingly, using the Wound Healing Device, all wound types, mechanical or thermal, acute or chronic, infected or sterile, may undergo healing more rapidly than similar wounds left to heal naturally or which are treated with currently available methods. In addition, the Wound Healing Device comprising a knitted mesh is suitable for use to prevent hernia formation following surgery, particularly abdominal surgery. A "therapeutically effective amount" of a therapeutic agent within the meaning of the present invention will be determined by a patient's attending physician or veterinarian. Such amounts are readily ascertained by one of ordinary skill in the art and will enable accelerated wound healing when administered in accordance with the present invention. Factors which influence what a therapeutically effective amount will be include, the specific activity of the therapeutic agent being used, the wound type (mechanical or thermal, full or partial thickness, surgical, etc.), the size of the wound, the wound's depth (if full thickness), the absence or presence of infection, time elapsed since the injury's infliction, and the age, physical condition, existence of other disease states (i.e. obesity and/or diabetes), and nutritional status of the patient. Additionally, other medication the patient may be receiving will effect the determination of the therapeutically effective amount of the therapeutic agent to administer.

EXAMPLES

The following examples are put forth so as to provide those of ordinary skill in the art with a complete disclosure and description of how to make and use the compositions and methods of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees centigrade, and pressure is at or near atmospheric.

Example 1

Preparation of AMP Cell Compositions

Amnion epithelial cells were dissociated from starting amniotic membrane using the dissociation agents PXXIII. The average weight range of an amnion was 18-27 g. The number of cells recovered per g of amnion was about 10-15× $10^6$ for dissociation with PXXIII.

Method of obtaining selected AMP cells—Amnion epithelial cells were plated immediately upon isolation from the amnion. After ~2 days in culture non-adherent cells were removed and the adherent cells were kept. This attachment to a plastic tissue culture vessel is the selection method used to obtain the desired population of AMP cells. Adherent and non-adherent AMP cells appear to have a similar cell surface marker expression profile but the adherent cells have greater viability and are the desired population of cells. Adherent AMP cells were cultured in basal medium supplemented with human serum albumin until they reached ~120,000-150,000 cells/cm$^2$. At this point, the cultures were confluent. Suitable cell cultures will reach this number of cells between ~5-14 days. Attaining this criterion is an indicator of the proliferative potential of the AMP cells and cells that do not achieve this criterion are not selected for further analysis and use. Once the AMP cells reached ~120,000-150,000 cells/cm$^2$, they were collected and cryopreserved. This collection time point is called p0.

Example 2

Generation of ACCS

The AMP cells of the invention can be used to generate ACCS, including pooled ACCS. The AMP cells were isolated as described above and ~1×10$^6$ cells/mL were seeded into T75 flasks containing ~10 mL culture medium as described above. The cells were cultured until confluent, the medium was changed and ACCS was collected 3 days post-confluence. Optionally, the ACCS is collected again after 3 days, and optionally again after 3 days. Skilled artisans will recognize that other embodiments for collecting ACCS from confluent cultures, such as using other tissue culture vessels, including but not limited to cell factories, flasks, hollow fibers, or suspension culture apparatus, etc. are also contemplated by the methods of the invention (see Detailed Description above). It is also contemplated by the instant invention that the ACCS be cryopreserved, lyophilized, irradiated or formulated for sustained-release following collection. It is also contemplated that ACCS be collected at different time points (see Detailed Description for details).

Example 3

Generation of Pooled ACCS

ACCS was obtained essentially as described above. In certain embodiments, ACCS was collected multiple times from an AMP culture derived from one placenta and these multiple ACCS collections were pooled together. Such pools are referred to as "SP pools" (more than one ACCS collection/one placenta). In another embodiment, AMP cultures were derived from several placentas, i.e. from 5 or 10 placentas. The AMP cells from each placenta were cultured and one ACCS collection from each culture was collected and then they were all pooled. These pools are termed "MP1 pools" (one ACCS collection/placenta, multiple placentas). In yet another embodiment, AMP cell cultures were derived from several placentas, i.e. from 5 or 10 placentas. The AMP cells from each placenta were cultured and more than one ACCS collection was performed from each AMP cell culture and then pooled. These pools are termed "MP2 pools" (more than one ACCS collection/placenta, multiple placentas).

Example 4

Production of PCS

The following PCS compositions are produced:
Composition A: VEGF and TIMP-1; Composition B: VEGF, Angiogenin and TIMP-1; Composition C: VEGF, Angiogenin, PDGF-BB and TIMP-1; Composition D: VEGF, Angiogenin, PDGF-BB, TGFβ2 and TIMP-1; Composition E: VEGF and TIMP-2; Composition F: VEGF, Angiogenin and TIMP-2; Composition G: VEGF, Angiogenin, PDGF-BB and TIMP-2; Composition H: VEGF, Angiogenin, PDGF-BB, TGFβ2 and TIMP-2; Composition I: VEGF, TIMP-1 and TIMP-2; Composition J: VEGF, Angiogenin, TIMP-1 and TIMP-2; Composition K: VEGF, Angiogenin, PDGF-BB, TIMP-1 and TIMP-2; Composition L: VEGF, Angiogenin, PDGF-BB, TGFβ2, TIMP-1 and TIMP-2; Composition M: Angiogenin and TIMP-1; Composition N: Angiogenin, PDGF-BB and TIMP-1; Composition 0: Angiogenin, PDGF-BB, TGFβ2 and TIMP-1; Composition P: Angiogenin and TIMP-2; Composition Q: Angiogenin, PDGF-BB and TIMP-2; Composition R: Angiogenin, PDGF-BB, TGFβ2 and TIMP-2; Composition S: Angiogenin, PDGF-BB, TGFβ2, TIMP-1 and TIMP-2; Composition T: PDGF-BB and TIMP-1; Composition U: PDGF-BB, TGFβ2 and TIMP-1; Composition V: PDGF-BB and TIMP-2; Composition W: PDGF-BB, TGFβ2 and TIMP-2; Composition X: PDGF-BB, TIMP-1 and TIMP-2; Composition Y: PDGF-BB, TGFβ2, TIMP-1 and TIMP-2.

VEGF, Angiogenin, PDGF-BB, TGFβ2, TIMP-1 and TIMP-2 are added at the following physiologic levels: ~5-16 ng/mL for VEGF, ~3.5-4.5 ng/mL for Angiogenin, ~100-165 pg/mL for PDGF, ~2.5-2.7 ng/mL for TGFβ2, ~0.68 µg mL for TIMP-1 and ~1.04 µg/mL for TIMP-2.

VEGF may be obtained from Invitrogen, catalog #PHG0144, PHG0145, PHG0146, PHG0141 or PHG0143; Angiogenin may be obtained from R&D Systems, catalog #265-AN-050 or 265-AN-250; PDGF-BB may be obtained from Invitrogen, catalog #PHG0044, #PHG0045, #PHG0046, #PHG0041, #PHG0043; TGFβ2 may be obtained from Invitrogen, catalog #PHG9114; TIMP-1 may be obtained from R&D Systems, catalog #970-TM-010; and TIMP-2 may be obtained from R&D Systems, catalog #971-TM-010.

VEGF, Angiogenin, PDGF-BB, TGFβ2, TIMP-1 and TIMP-2 are added to a carrier such as normal saline, PBS, lactated Ringer's solution, cell culture media, or other suitable aqueous solutions known to skilled artisans.

Example 5

Production of Wound Healing Device

The Wound Healing Device of the invention is made by adsorbing onto a nonabsorbable or bioerodable braided suture or knitted mesh CFC, including ACCS, concentrated ACCS, PCS, or concentrated PCS. Suitable braided sutures are available commercially (non-limiting examples include bioerodable sutures such as DEXON™ S braided absorbable suture and POLYSORB™ coated braided suture, and nonabsorbable sutures such as SURGILON™, SURGIDAC™, Tlo CRON™, Covidien, Norwalk, Conn. 06856, USA). Suitable knitted mesh is available commercially from Ethicon, Inc., Somerville, N.J. (for example, Vicryl™ Knitted Mesh (Polyglycan 910).

The CFC, including ACCS, concentrated ACCS, PCS, or concentrated PCS, may be adsorbed as a liquid onto the braided sutures or knitted mesh or may be subjected to alternative formulation prior to absorption. Alterative formulations include sustained-release/controlled-release/timed-release as described in detail elsewhere in the specification. Also contemplated are formulations in which gelling or thickening agents such as human serum albumin, hyaluronic acid, or collagen are added to the CFC, including ACCS, concentrated ACCS, PCS, or concentrated PCS. Such agents increase the ability of the CFC, including ACCS, concentrated ACCS, PCS, or concentrated PCS to adsorbed onto the surface or be released from the surface.

The Wound Healing Device may be packaged with the suture or knitted mesh and the CFC, including ACCS, concentrated ACCS, PCS, or concentrated PCS already adsorbed onto it or it may be packaged with the two components packaged separately and then combined just prior to use.

Example 7

Adsorption of ACCS onto Sutures and Subsequent Release of Proteins Off of the Sutures The purpose of this experiment was to evaluate the ability of various sutures to adsorb ACCS and to evaluate the ability for proteins contained in ACCS to elute from the sutures. Two types of sutures were tested in this study: Size 1 DEXON™ S (Covidien, Norwalk, Conn.) and Size 1 MERSILENE™ (Ethicon, Inc., Somerville, N.J.). Both sutures were uncoated since it was determined in a previous experiment that coated sutures inhibit the adsorption of liquid. DEXON™ is an absorbable suture and MERSILENE™ is a non-absorbable polyester suture. Each type of suture was placed in 50× concentrated ACCS for 30 minutes. The sutures were then rinsed for various time periods and the rinses were analyzed by ELISA to determine the amount of ACCS adsorbed or released. ELISA results for Angiogenin and TIMP-2 showed that both types of suture adsorb and release the ACCS proteins. DEXON™ S appeared to release more ACCS into the rinses. The exact amount of adsorption was unclear in this experiment, however, it appears that each 10 cm piece of suture released between 5-6.5 µL of 50× ACCS in 15 minutes.

Example 6

Evaluation of the Wound Healing Device in an Animal Model

One object of the invention is to decrease wound failure in surgical and traumatic injuries by treating these acute wounds with the wound healing device. Mechanically, failing abdominal laparotomy incisions form incisional hernias. Clinically, this manifests as defects in the musculo-tendinous-peritoneal layer of the abdominal wall. Thus focusing on muscle, fascial and skin healing is important. The serious clinical consequences of such failures are acute abdominal wall dehiscence and evisceration, the incarceration and obstruction of peritoneal viscera, loss of the ability of the abdominal wall to maintain torso posture, and chronic pain.

The purpose of the experiment is to evaluate the ability of the wound healing device to reduce or prevent hernia formation in an animal model of incisional hernia. The experiment will utilize male Sprague-Dawley rats which will be subjected to abdominal incision and then treated with the wound healing device or appropriate controls. At the end of the study period, post euthanasia, a 5×10 cm section of the abdominal wall will be excised from each animal. The muscle will be stretched out and pinned on a dissecting board (on each of the four corners) with the peritoneal side facing upwards. A ruler, along with individual identifiers, will be placed next to each sample and a standardized picture will be taken equi-distance from each sample to ensure appropriate scaling. The presence or absence of hernia will be observed and hernia size will be measured The present invention may be embodied in other specific forms without departing from the spirit or essential attributes thereof. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Throughout the specification various publications have been referred to. It is intended that each publication be incorporated by reference in its entirety into this specification.

What is claimed is:

1. A wound healing device for healing incisional wounds comprising a suture or knitted mesh which is embedded with a wound healing composition, wherein the wound healing composition comprises protein factors selected from the group consisting of physiologic levels of VEGF, Angiogenin, PDGF, TGFβ2, TIMP-1 and TIMP-2 that are dissolved in an aqueous solution, wherein the physiologic levels are ~5-16 ng/mL for VEGF, ~3.5-4.5 ng/mL for Angiogenin, ~100-165 pg/mL for PDGF, ~2.5-2.7 ng/mL for TGFβ2, ~0.68 μg mL for TIMP-1 and ~1.04 μg/mL for TIMP-2.

2. The wound healing device of claim 1 wherein the wound healing composition is Amnion-derived Cellular Cytokine Solution (ACCS).

3. The wound healing device of claim 1 wherein the suture or knitted mesh is braided.

4. The wound healing device of claim 1 which is contained in a sterile package.

5. The wound healing device of claim 1 wherein the suture is nonabsorbable or bioerodable and the knitted mesh is bioerodable.

6. The wound healing device of claim 5 wherein the bioerodable suture or knitted mesh is made of polyglycolic acid, polyglutamic acid, polydioxanone, polylactide, or caprolactone.

7. The wound healing device of claim 5 wherein the nonabsorbable suture is made of nylon, polyester, polypropylene or silk.

* * * * *